(12) United States Patent
Buelow et al.

(10) Patent No.: US 12,299,878 B2
(45) Date of Patent: May 13, 2025

(54) WORKLOAD REDUCER FOR QUALITY AUDITORS IN RADIOLOGY

(71) Applicant: KONINKLIJKE PHILIPS N.V., Eindhoven (NL)

(72) Inventors: Thomas Buelow, Grosshansdorf (DE); Tim Philipp Harder, Ahrensburg (DE); Stewart Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 364 days.

(21) Appl. No.: 17/770,759

(22) PCT Filed: Oct. 27, 2020

(86) PCT No.: PCT/EP2020/080089
§ 371 (c)(1),
(2) Date: Apr. 21, 2022

(87) PCT Pub. No.: WO2021/083847
PCT Pub. Date: May 6, 2021

(65) Prior Publication Data
US 2022/0375081 A1  Nov. 24, 2022

Related U.S. Application Data

(60) Provisional application No. 62/926,586, filed on Oct. 28, 2019.

(51) Int. Cl.
*G06T 7/00* (2017.01)
*G06T 7/13* (2017.01)
*G06T 7/194* (2017.01)

(52) U.S. Cl.
CPC .............. *G06T 7/0012* (2013.01); *G06T 7/13* (2017.01); *G06T 7/194* (2017.01);
(Continued)

(58) Field of Classification Search
CPC ......... G06T 7/0012; G06T 7/13; G06T 7/194; G06T 2207/10116; G06T 2207/30068;
(Continued)

(56) References Cited

U.S. PATENT DOCUMENTS 8,300,908 B2 * 10/2012 Schneider ............. G06T 7/0012
382/128
11,132,793 B2 * 9/2021 Sainz de Cea ........ G16H 30/40
(Continued)

FOREIGN PATENT DOCUMENTS

WO    WO2012107057 A1    8/2012
WO    WO2018015911 A1    1/2018

OTHER PUBLICATIONS

European recommendations for the quality of breast cancer screening and diagnosis. Fourth edition 2008 (Year: 2008).*
(Continued)

*Primary Examiner* — Juan A Torres (57) ABSTRACT

An apparatus (10) for manually auditing a set (30) of images having quality ratings (38) for an image quality metric assigned to the respective images of the set of images by an automatic quality assessment process (40) includes at least one electronic processor (20) programmed to: generate quality rating confidence values (42) indicative of confidence of the quality ratings for the respective images; select a subset (32) of the set of images for manual review based at least on the quality rating confidence values; and provide a user interface (UI) (27) via which only the subset of the set of images is presented and via which manual quality ratings (46) for the image quality metric are received for only the subset of the set of images.

15 Claims, 5 Drawing Sheets

(52) U.S. Cl.
CPC ............... *G06T 2207/10116* (2013.01); *G06T 2207/30068* (2013.01); *G06T 2207/30168* (2013.01)

(58) Field of Classification Search
CPC . G06T 2207/30168; G06T 2207/10081; G06T 2207/10088; G06T 2207/10104; G06T 2207/10108; G06T 2207/10132; G06T 7/12; G06T 7/187; G06T 5/20; G16H 40/20; G16H 30/40
USPC ........................................................ 382/128
See application file for complete search history.

(56) References Cited

U.S. PATENT DOCUMENTS

| | | |
|---|---|---|
| 2002/0188652 A1 | 12/2002 | Goldhaber |
| 2005/0251013 A1 | 11/2005 | Krishnan |
| 2006/0221402 A1 | 10/2006 | Jiang |
| 2006/0274145 A1 | 12/2006 | Reiner |
| 2014/0126790 A1 | 5/2014 | Duchesne |
| 2016/0203600 A1 | 7/2016 | Abdolell |
| 2016/0256126 A1 | 9/2016 | Wehnes |
| 2018/0101644 A1 | 4/2018 | Hammes |
| 2019/0261938 A1 | 8/2019 | Sevenster |
| 2021/0279919 A1* | 9/2021 | Wang .................... G06T 7/0014 |
| 2023/0071400 A1* | 3/2023 | Abdolell ................ G16H 30/20 |

OTHER PUBLICATIONS

PCT International Search Report, International application No. PCT/EP2020/080089, Mar. 23, 2021.

Bulow T. et al., "Automatic Assessment of the Quality of Patient Positioning in Mammography", SPIE—Medical Imaging 2013, Computer-Aided Diagnosis, vol. 8670, 867024, 2013.

Buelow T. et al., "Automatic Assessment of the Quality of Patient Positioning and Field of View of Head CT Scans", Proceedings of SPIE, SPIE Medical Imaging, San Diego, CA, 2019.

\* cited by examiner

WORKLOAD REDUCER FOR QUALITY AUDITORS IN RADIOLOGY

CROSS-REFERENCE TO PRIOR APPLICATIONS

This application is the U.S. National Phase application under 35 U.S.C. § 371 of International Application No. PCT/EP2020/080089, filed on Oct. 27, 2020, which claims the benefit of US Provisional Patent Application Ser. No. 62/926,586, filed on Oct. 28, 2019. These applications are hereby incorporated by reference herein.

FIELD

The following relates generally to the radiology arts, imaging arts, imaging workflow arts, automated radiology auditing arts, imaging workflow training arts, mammography arts, skin fold detection arts, and related arts.

BACKGROUND

Presently, governmental regulations in most regulatory jurisdictions require that quality assurance assessments of radiology practices be performed by auditors skilled in the visual assessment of radiology images. The auditors review a random sampling of images produced by the radiology practice. The quality assessment calls for the auditors to make quality assessments respective to various features. For example, in mammography the assessed features may include correct positioning of the breast, presence/absence of skin folds, and so forth. In magnetic resonance imaging (MRI), the various features may include appropriate selection of certain scan parameters such as echo time (TE), proper placement of the patient inside the MRI bore, and so forth. In order to assure that radiology departments are operating at a sufficient level of quality, institutions submit samples of their images for auditing in order to remain certified.

For example, an efficient mammography screening requires an adherence to regulatory rules relating to image quality. Quality requirements related to patient positioning are well defined in clinical guidelines along with image-based criteria, and these guidelines therefore allow for independent evaluation by experts. Many of these criteria lend themselves to automated, computerized evaluation in a rather straightforward manner. This is true, for example, for criteria that relate to geometric location and relative position of anatomic landmarks such as the nipple, inframammary angle and the contour of the pectoral muscle.

However, regulatory oversight has become more stringent in many jurisdictions, in particular often calling for a higher proportion of images to be audited and shortened intervals between audits in order to maintain regulatory compliance. More stringent oversight increases the workload on the auditors. This workload could be alleviated by applying automated quality assessment algorithms to score images with respect to the various features. However, the accuracy of automated quality assessment algorithms can be limited, making them unsuitable as an exclusive means for regulatory auditing tasks.

The following discloses certain improvements to overcome these problems and others.

SUMMARY

In one aspect, an apparatus for manually auditing a set of images having quality ratings for an image quality metric assigned to the respective images of the set of images by an automatic quality assessment process includes at least one electronic processor programmed to: generate quality rating confidence values indicative of confidence of the quality ratings for the respective images; select a subset of the set of images for manual review based at least on the quality rating confidence values; and provide a user interface (UI) via which only the subset of the set of images is presented and via which manual quality ratings for the image quality metric are received for only the subset of the set of images.

In another aspect, an apparatus includes at least one electronic processor programmed to detect skin folds in a mammogram image by a skin fold detection method including: filtering the mammogram image using an edge detection filter to generate an edge filtered image; detecting, in the edge filtered image, one or more significant edges each having a length exceeding a minimum length; and identifying a skin fold as a significant edge that satisfies a skin fold criterion.

In another aspect, an imaging method includes: retrieving, for manually auditing, a set of images having quality ratings for an image quality metric assigned to the respective images of the set of images by an automatic quality assessment process; generating quality rating confidence values indicative of confidence of the quality ratings for the respective images; selecting a subset of the set of images for manual review based at least on the quality rating confidence values; providing a UI via which only the subset of the set of images is presented and via which manual quality ratings for the image quality metric are received for only the subset of the set of images; and perform the automatic quality assessment process on the images of the set of images to assign the quality ratings to the respective images of the set of images by operations including: for each image, applying an edge detection filter to the image to generate an edge filtered image; detecting significant edges in the edge filtered image as edges having length greater than a minimum length; and identifying skin folds as significant edges that satisfy a skin fold criterion, wherein the quality rating is assigned on the basis of presence or absence of identified skin folds.

One advantage resides in providing an imaging auditing process that employs automated quality assessment of limited accuracy in the auditing without sacrificing accuracy of the auditing process.

Another advantage resides in providing such an image auditing process that advantageously dynamically improves the automated quality assessment.

Another advantage resides in automatically detecting skin folds in mammogram images, with the disclosed automatic skin fold detector being suitable for use in embodiments of the disclosed image auditing process and/or as a quality check during clinical mammography procedures.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Systems disclosed herein leverage an automatic image quality assessment algorithm to perform robust auditing, even if the automated image quality assessment is not sufficiently accurate to perform automated auditing. In some embodiments disclosed herein, a system is disclosed for selecting a subset of the automatically audited images for manual review/confirmation. One way to do this might be to randomly select a portion of the automatically audited images for subsequent manual review. However, if the automatic image quality assessment is reasonably accurate, then this would be inefficient as most of the images that are manually reviewed would be found to have been correctly assessed by the automatic image quality assessment. To provide better use of human auditors' time, in one approach, the output of the quality assessment algorithm is analyzed to generate a confidence value indicative of a confidence of the assessment. For example, if the quality assessment algorithm operates by generating a score and making a decision based on comparison of the score with a threshold, then the confidence value may be based on how close the score is to the threshold, with a score that is close to the threshold indicating a low confidence whereas as score that is well above (or well below) the threshold has high confidence. The portion of the automatically audited images selected for subsequent manual review can then be selected as those images for which the automatic image quality assessment has low confidence. In this way, the efforts of the human auditors are efficiently targeted to the more difficult image assessments, since the images for which the automatic image quality assessment has high confidence are likely to have been accurately assessed.

Alternatively, if the quality assessment algorithm optimizes an objective function (i.e. "figure of merit") to make the quality assessment, then an analysis of curvature of the objective function or the presence of local maxima in the objective function can provide the confidence value. In this approach, a broad maximum may translate to low confidence whereas a sharply peaked maximum translates to high confidence, and/or significant local maxima may reduce confidence. Other types of confidence metrics may be generated based on the particulars of the automated quality assessment algorithm. In another, not necessarily mutually exclusive, approach, prior knowledge of image features that make quality assessment challenging may be detected in the image and used to identify automated quality assessments of low confidence.

The subset of images for manual audit of a particular quality assurance feature are selected as a subset of the images for which the automatically generated quality assessment score has lowest confidence. However, reliability of this selection assumes that the confidence scores are themselves correct. If this is not the case, then the subset selected for manual audit may not be the images that are most difficult for the automated quality assessment. To address this, in a variant approach, this subset of images with lowest confidence may be augmented by a subset generated as a random sampling of images processed by the automated image assessment. This latter approach provides a check on the accuracy of the automatic selection process—if human auditors reverse the quality assurance assessment for the random samples more often than for the set chosen based on low confidence value then this may indicate that the approach for confidence value assignment may need to be adjusted.

The disclosed quality assessment systems can in general be employed in conjunction with any imaging modality and any automated image assessment. The illustrative examples relate to mammography images, and in particular employ a skin fold detector system that is disclosed herein. The disclosed skin fold detector is a quality assurance algorithm for assessment of the feature of presence/absence of skin folds in the mammogram image. Such skin folds can arise because during a mammography examination, the breast is compressed by compression plates to improve the image quality. The breast compression is performed by the imaging technician, and if not done properly then a skin fold (or multiple skin folds) can be created. These skin folds can obscure breast lesions so as to produce a false negative result, or can contribute to misinterpretation of an image feature as a breast lesion leading to a false positive result. The disclosed skin fold detection approach applies an edge filter to the mammogram image to highlight the edges. Significant edges detected in the edge-filtered image are identified, and the significant edges are scored as to likelihood of being skin folds. Optionally, the image (prior to edge filtering) is segmented into four areas: background, pectoral muscle, adipose tissue, and fibro-glandular tissue. Breast cancer tumors are expected to occur predominantly in the fibro-glandular tissue, though they may also occur in adipose or pectoral muscle tissue as well. Hence, the scoring of the significant edges can optionally include the type(s) of tissue through which the edges pass as part of the significant edge scoring criterion.

In one illustrative approach, connectivity analysis is applied to the edge filtered image to detect contiguous edges of some minimum length. Based on the area segmentation, any expected edges are discarded from further analysis. These are typically edges delineating the boundaries of the segmented areas. Remaining edges are scored as to likelihood of being a skin fold. The illustrative embodiments employ three scoring criteria: (i) length of the edge (longer is more likely to be a skin fold); (ii) contrast of the edge (higher contrast is more likely to be a skin fold; note that edge contrast typically translates to edge intensity in the edge filtered image); and (iii) the area within which the edge occurs (edges in only the pectoral muscle or adipose tissue score lower than edges that pass through fibro-glandular tissue since the latter is more likely to obscure a malignant tumor). Edges that score higher than a threshold are identified as likely skin folds.

The skin fold detector may be used as the automated image assessment in the context of the disclosed auditing system, and/or may be used elsewhere. For example, during clinical mammography procedures, each acquired mammogram image may be assessed by the skin fold detector, and if a possible skin fold is detected then the technologist is alerted that the image should be retaken after repositioning the breast. Additionally or alternatively, the skin fold detector may be considered to be an example of an automated quality assessment algorithm in the context of the workload reducer. In this case, the confidence value may be assigned based on how close the score of the highest-scoring edge is to the threshold—if it is close to the threshold then this may be considered to be a low confidence skin fold assessment.

While the following is primarily described in the context of mammography, the disclosed systems and methods are implementable in other imaging modalities such as computed tomography (CT), magnetic resonance imaging (MRI), or other modalities. In a particular example, the skin fold detector is specific to mammography.

Figure 1:
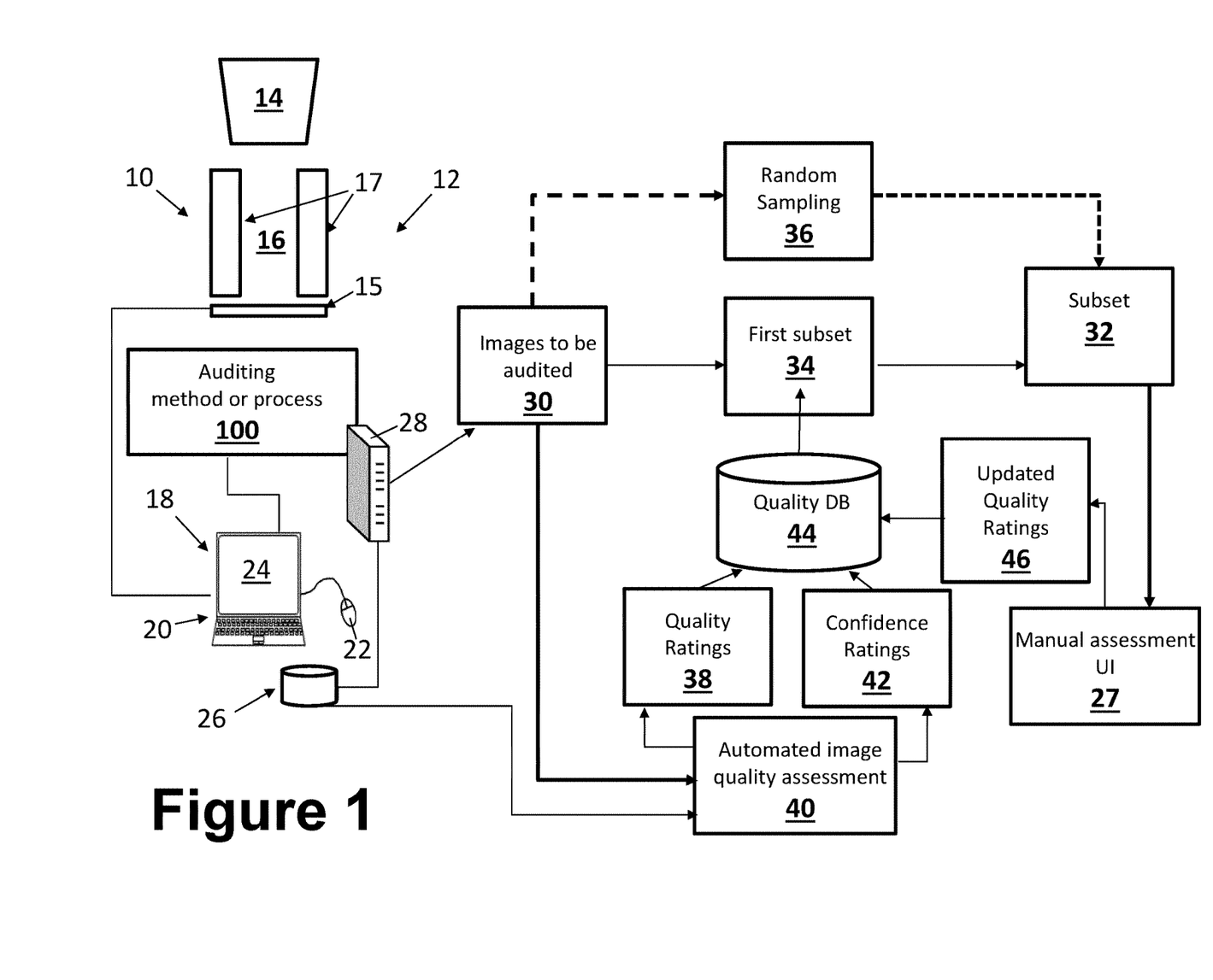
FIG. 1 diagrammatically illustrates an illustrative apparatus for manually auditing a set of images in accordance with the present disclosure.

With reference to FIG. 1, an illustrative apparatus 10 for manually auditing images generated by an image acquisition device (also referred to as an imaging device) 12. The illustrative image acquisition device 12 is a diagrammatically shown mammography imaging device, but can be any suitable imaging device modality, such as Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 12 may also be a hybrid imaging device such as a PET/CT or SPECT/CT imaging system.

The illustrative mammography device includes an X-ray source 14 containing an X-ray tube (detail not shown), an X-ray detector array 15 arranged to detect the X-ray beam emitted by the X-ray source 14 after passing through an examination region 16, and compressor plates 17 that are used to compress the breast for the mammography imaging. Other common components are not shown, such as a rack for adjusting the height of the various components and hardware for rotating/arranging positions of the compressor plates 17 and possibly other components in order to compress the breast in various orientations, e.g. mediolateral compression, craniocaudal compression, and/or so forth. It should be noted that while the image acquisition device 12 is shown as an illustrative example, more generally the auditing system may be applied to audit images generated by a number of imaging devices. For example, a mammography practice may have two, three, four, or more mammography units 12, and the auditing system may be applied to audit the images generated by all these mammography units 12. In the case of auditing a network of hospitals the database of audited images may be generated by dozens or more different imaging devices. Moreover, the auditing apparatus 10 need not include any imaging device 12, e.g. the auditing device may be a service provider that contracts with hospitals or other medical institutions, or with a government, to provide auditing services using the auditing apparatus.

FIG. 1 also shows an electronic processing device 18, such as a workstation computer, or more generally a computer. Alternatively, the electronic processing device 18 can be embodied as a server computer or a plurality of server computers, e.g. interconnected to form a server cluster, cloud computing resource, or so forth. The workstation 18 includes typical components, such as an electronic processor 20 (e.g., a microprocessor), at least one user input device (e.g., a mouse, a keyboard, a trackball, and/or the like) 22, and a display device 24 (e.g. an LCD display, plasma display, cathode ray tube display, and/or so forth). In some embodiments, the display device 24 can be a separate component from the workstation 18.

The electronic processor 20 is operatively connected with one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 18, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a visualization of a graphical user interface 27 for display on the display device 24.

The apparatus 10 also includes, or is otherwise in operable communication with, a database 28 storing a set 30 of images to be audited. The database 28 can be any suitable database, including a Radiology Information System (RIS) database, a Picture Archiving and Communication System (PACS) database, an Electronic Medical Records (EMR) database, and so forth. Alternatively, the database 28 can be implemented in the non-transitory medium or media 26. The workstation 18 can be used to access the stored set 30 of images to be audited, along with relevant information of the images to be audited (e.g., the scheduling information, the procedure description, the patient information, and so forth). In the case of providing auditing as a service, the database 28 may be maintained by the auditing service provider, and the images 30 are then received from a client (e.g. a hospital) and stored at the database 28.

The apparatus 10 is configured as described above to perform an imaging auditing workload reduction method or process 100. The non-transitory storage medium 26 stores instructions which are readable and executable by the at least one electronic processor 20 to perform disclosed operations including performing the imaging auditing workload reduction method or process 100. In some examples, the method 100 may be performed at least in part by cloud processing.

Figure 2:
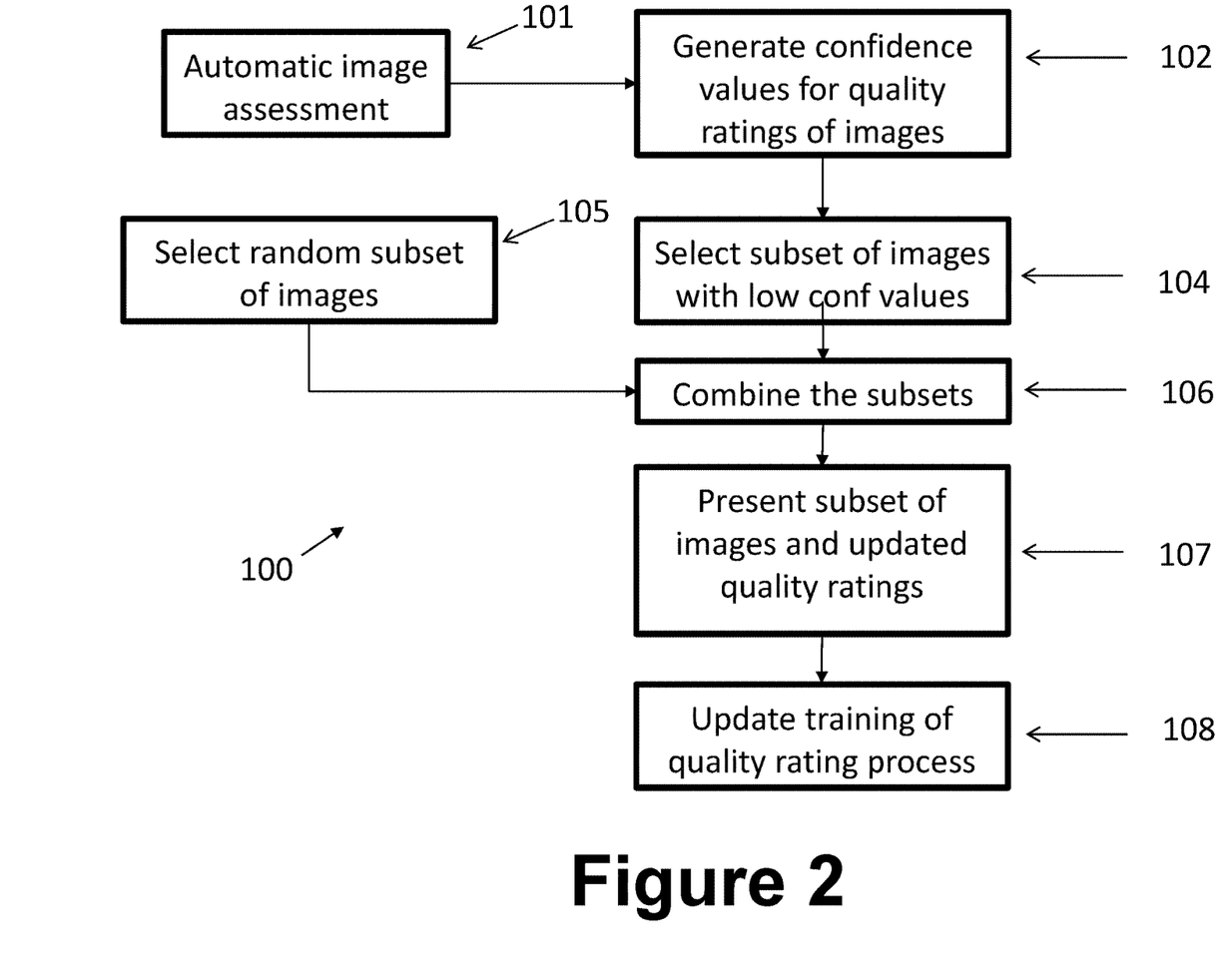
FIG. 2 shows exemplary flow chart operations performed by the apparatus of FIG. 1.

With continuing reference to FIG. 1 and with further reference to FIG. 2, an illustrative embodiment of the imaging auditing workload reduction method 100 is diagrammatically shown as a flowchart 100 in FIG. 2, while the righthand side of FIG. 1 diagrammatically shows the data flow. To begin the method 100, the set 30 of images to be audited are retrieved from the database 28. The set 30 of images to be audited are initially reviewed in an operation 101 by an automatic quality assessment process 40 (e.g. performed by the workstation 18 or another electronic processing device). Each respective image in the set 30 of images to be audited has a quality rating 38 for an image quality metric (e.g., presence/absence of skin folds) assigned to the image by the automatic quality assessment process 40. The quality rating 38 may be a binary value (e.g. "pass"=no skin fold detected or "fair"=a skin fold detected) or a scale value (e.g. an image quality metric may be rated on a scale of 1-5, or as a percentage value in the range 0-100% or so forth). The quality ratings 38 can be stored in a quality database 44 implemented in the one or more non-transitory computer readable medium 26.

In one example, the automated quality assessment 40 for mammography auditing may determine anatomical landmarks (e.g., nipple location, skin-line, contour of the pectoral muscle, and so forth). Based on the geometric relations and appearance of these landmarks, criteria for the quality of the images are evaluated and aggregated into an overall quality score 38 (which can be stored in the one more non-transitory computer readable medium 26). Another illustrative automatic quality assessment process 40 is the skin fold detector which is described elsewhere herein. In general, the automatic image assessment operation 101 (FIG. 2) is performed using one or more automated quality assessments 40 that are tailored to the imaging modality and the particular image feature or features that are to be audited.

At an operation 102, the at least one electronic processor 20 is programmed to generate quality rating confidence values 42 indicative of confidence of the quality ratings 38 for the respective images in the set 30 of images. The quality rating confidence value 42 for a given image provides a measure of how likely it is that the quality rating 38 for that image is correct. The operation 102 can be performed in a variety of ways, depending upon the architecture of the automatic quality assessment process 40.

In one embodiment, the automatic quality assessment process 40 assigns the quality rating 38 for a respective image in the set 30 of images by comparing a threshold with a figure of merit computed for the image. As a nonlimiting illustration, the figure of merit can be maximized using an anatomy detection algorithm. In one specific example, a contour of a pectoral muscle could be identified as a mean absolute gradient along a contour. In such cases of the automatic quality assessment process 40 employing a thresholding architecture, in the operation 102, the at least one electronic processor 20 is suitably programmed to generate the quality rating confidence value 42 for the image based on an absolute value of the difference between the threshold and the figure of merit for the image. The quality rating confidence value 42 is monotonically nondecreasing with increasing absolute value of the difference (e.g., the confidence value does not get smaller as the absolute value of the difference increases). This approach is premised on the expectation that, if the figure of merit is much larger than the threshold (large absolute value of the difference) then the quality rating is likely to be correct since even a relatively large error in the figure of merit will not be sufficient to take it below the threshold. Likewise, if the figure of merit is much smaller than the threshold (again yielding a large absolute value of the difference) then the quality rating is again likely to be correct since even a relatively large error in the figure of merit will not be sufficient to take it below the threshold. On the other hand, if the figure of merit is close to the threshold, whether slightly above the threshold or slightly below the threshold, then this yields a small absolute value of the difference. Here the quality rating is most likely to be incorrect, since a relatively small error in the figure of merit can take it across the threshold and change the resulting quality rating 38.

In another embodiment of the operation 102, the automatic quality assessment process 40 assigns the quality rating 38 for the image in the set 30 of images by a process including iteratively optimizing (e.g., minimizing or maximizing) a figure of merit computed for the image. For such an architecture, in the operation 102, the at least one electronic processor 20 is suitably programmed to generate the quality rating confidence value 42 for the image based on a derivative of the optimized figure of merit for the image, or more generally based on a peak sharpness of the optimized figure of merit for the image. This approach is premised on the expectation that a reliable quality rating 38 should be associated with a well-defined, sharp peak; whereas, an unreliable quality rating 38 is likely to be associated with a shallow or ill-defined peak.

In another suitable approach for architectures that optimize a figure of merit to determine the quality rating 38, in the operation 102, the automatic quality assessment process 40 generates the quality rating confidence value 42 for the image based on a number of local extrema of the figure of merit throughout a parameter space of the figure of merit. A high ratio of the maximal value to the second largest local maximum is used as measure of confidence in this example. This is premised on the expectation that if there is a central peak that dominates over all other peaks, then this is likely to be the correct result, whereas if there are a number of local extrema of similar size then an error is more likely.

In yet another embodiment of the operation 102, the at least one electronic processor 20 is programmed to generate the quality rating confidence value 42 for the image in the set 30 of images based on whether the image contains an image feature known to adversely impact accuracy of the automatic quality assessment process 40 (e.g., blurriness, anatomical region, and so forth). It will be appreciated that these are merely non-limiting examples, and other approaches for determining the quality rating confidence value 42 may be appropriate depending upon the architecture of the automatic quality assessment process 40. In addition, the operation 102 is repeated for each image in the set 30 of images to be audited.

At an operation 104, the at least one electronic processor 20 is programmed to select a (first) subset 34 of the set 30 of images for manual review based at least on the quality rating confidence values. The selection of the first subset 34 of the set 30 of images for manual review is based on the quality rating confidence values. The first subset 34 can be selected as images having a confidence value 42 below a predetermined confidence threshold, that should therefore be reviewed manually.

Optionally, in an operation 105 a random sampling 36 of the set 30 of images is selected, and in an operation 106 the first subset 34 is then combined with a random sampling 36 of the set 30 of images to generate the subset 32 of images for manual review. The optional random sampling 36 beneficially allows for detection of unexpected deficiencies of the confidence value algorithms employed in the operation 102. (In other embodiments, the random sampling is omitted, and the (first) subset 34 forms the complete subset 32 of images for manual review).

At an operation 107, the at least one electronic processor 20 is programmed to provide the UI 27 on the display 24 via which only the subset 34 of the set of images is presented and via which manual quality ratings 46 for the image quality metric are received for only the subset 32 of the set of images. The subset 32 of images is reviewed and rated manually by a human. The manual quality ratings 46 are updates of the quality ratings 38 generated by the automatic image quality assessment process 40. The updated quality ratings 46 can be stored in the non-transitory computer readable medium 26.

At an optional operation 108, the at least one electronic processor 20 is programmed to perform update training of the automatic quality assessment process 40 using the subset 32 of the set of images and the manual quality ratings 46 received via the UI 27. The manual quality ratings 46 can be retrieved from the non-transitory computer readable medium 26 during the automatic quality assessment process 40 for a new set 30 of images to be audited. The at least one electronic processor 20 can implement a learning module to adapt the manual quality ratings 46 to the set 30 of images.

Figure 3:
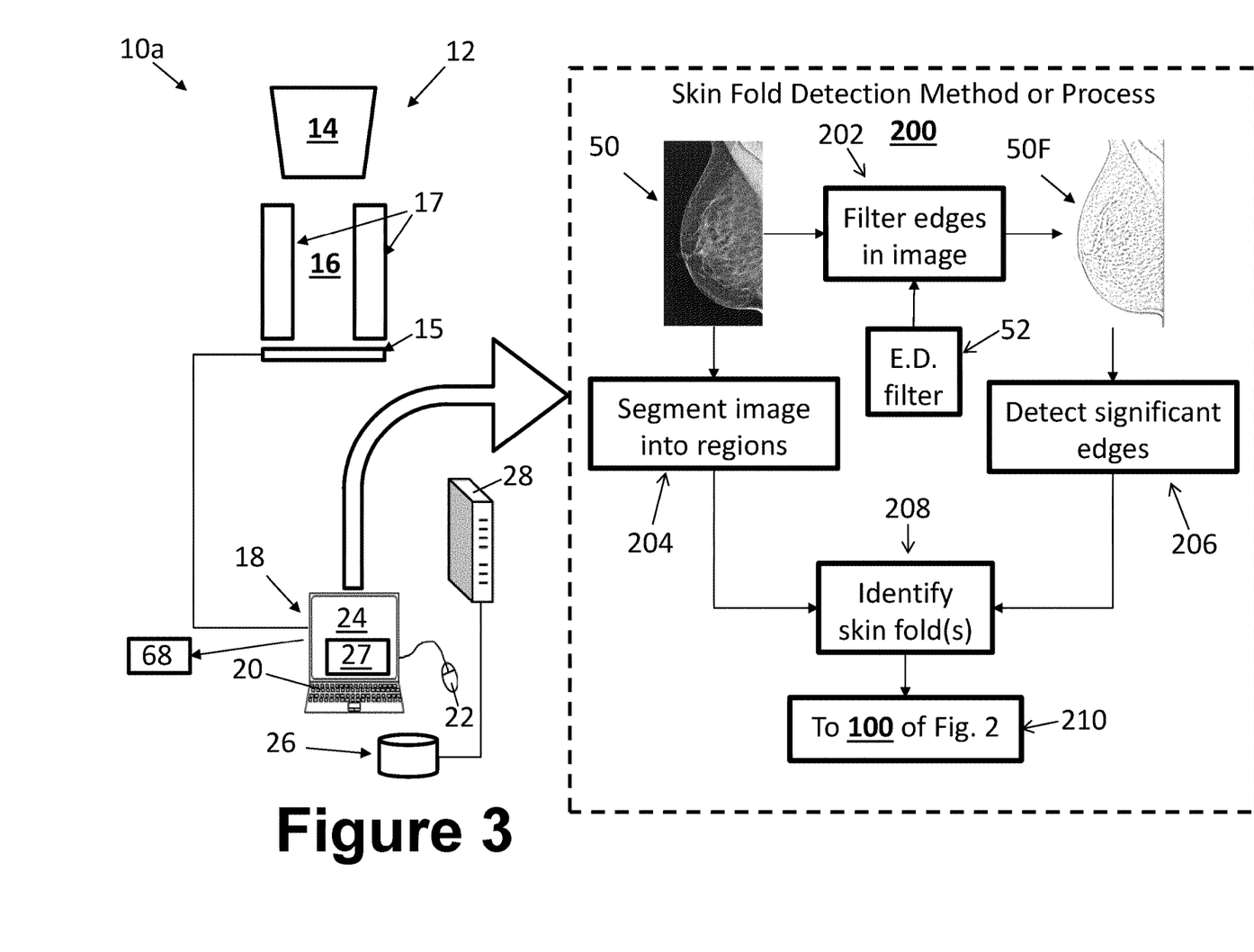
FIG. 3 shows another embodiment of the apparatus of FIG. 1.

Referring now to FIG. 3, a skin fold detector for use in assessing mammography images is described, which may for example be used as the automatic quality assessment process 40 if the image quality feature to be audited is presence/absence of skin folds. In FIG. 3, an apparatus 10a is operatively connected to a mammography device 12 including the X-ray source 14 and detector 15 arranged to image a breast in an examination region 16 that is compressed by compressor plates 17 is described. The apparatus 10a includes the workstation 18 which is configured as described in referring to FIG. 1 and is programmed to perform a skin fold detection method or process 200. The non-transitory storage medium 26 stores instructions which are readable and executable by the at least one electronic processor 20 to perform disclosed operations including performing the skin fold detection method or process 200. In some examples, the method 200 may be performed at least in part by cloud processing.

Figure 4:
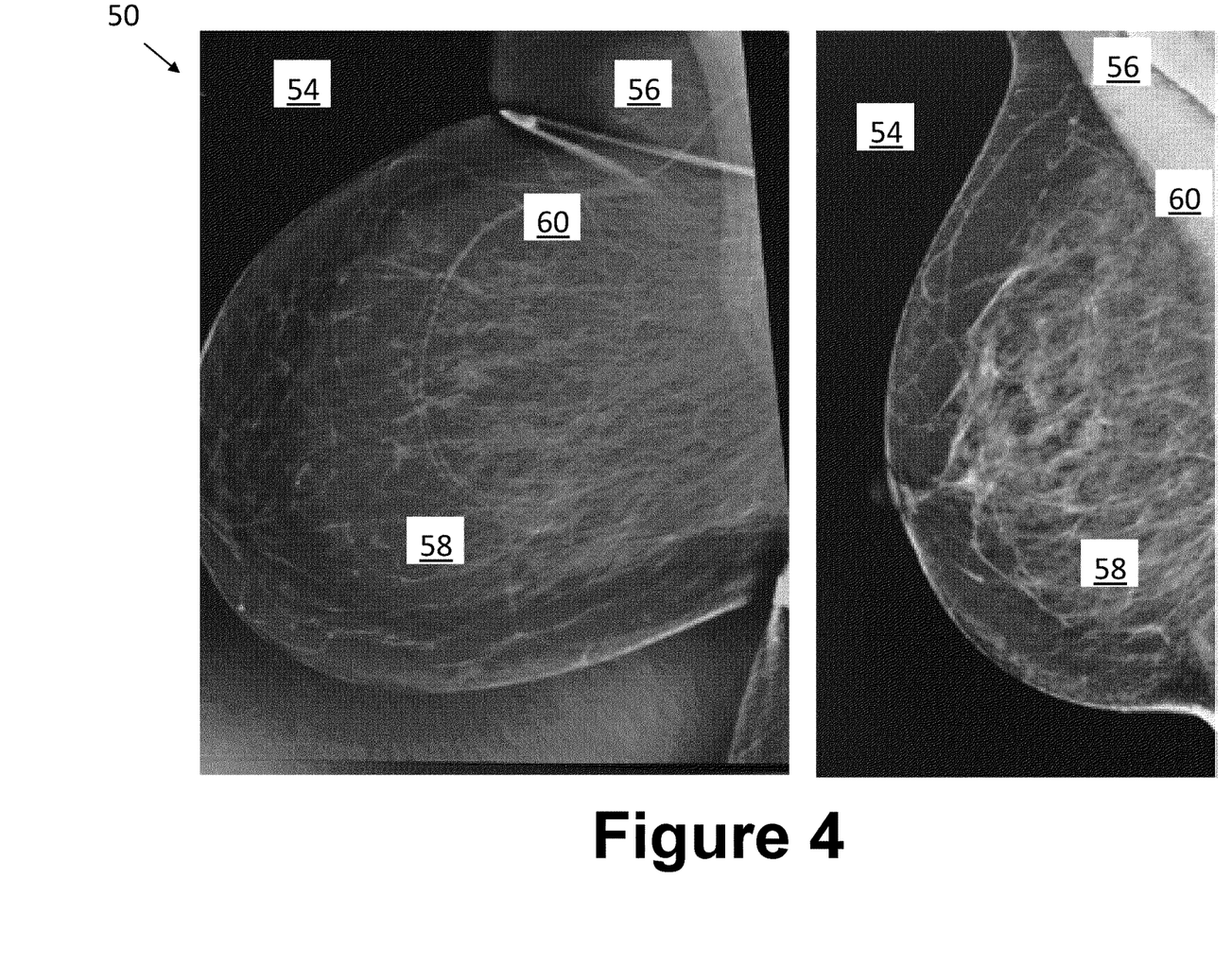
FIG. 4 shows two illustrative mammography images.
Figure 5:
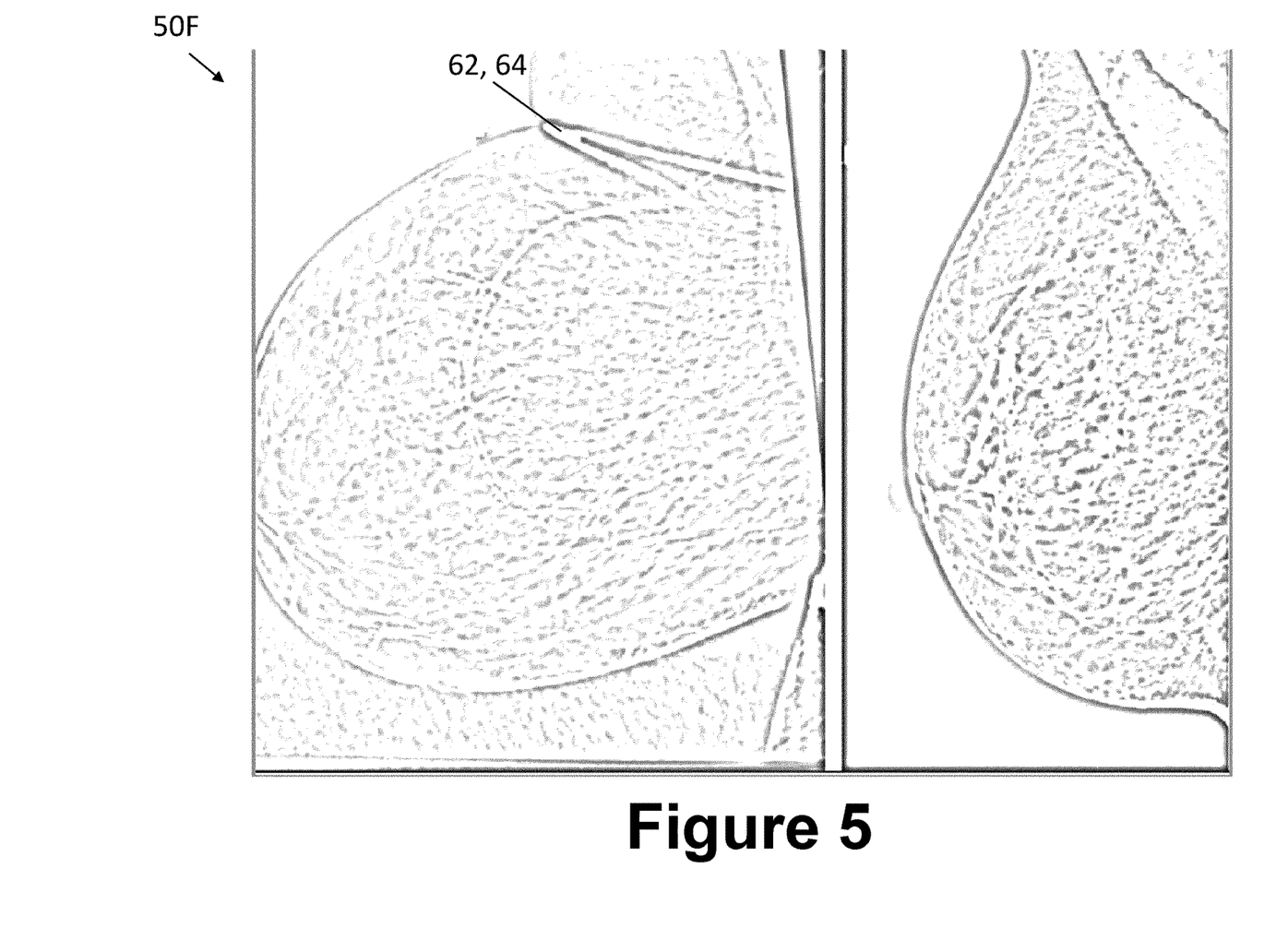
FIG. 5 shows the illustrative mammography images of FIG. 4 after processing by an example of an image analyzed by the apparatus of FIG. 3.

With continuing reference to FIG. 3, and with reference to FIGS. 4 and 5, an illustrative embodiment of the skin fold detection method 200 is diagrammatically shown as a flowchart. To begin the method 200, one or more mammography images 50 (two illustrative images 50 are shown in FIG. 4) are acquired by the mammography device 12 and stored in the database 28. Although the following will be described in reference to one mammography image 50, it will be appreciated that the method 200 can be applied to multiple mammography images. At an operation 202, the at least one electronic processor 20 is programmed to filter the mammography image 50 using an edge detection filter 52 to generate an edge filtered image. The edge detection filter 52 can be any suitable edge detection algorithm known in the art (e.g., a difference of Gaussians edge detector or so forth), and can detect edges exhibiting a high image gradient. The output of the operation 202 is an edge-filtered image 50F corresponding to the original image 50. FIG. 5 illustrates edge filtered images corresponding to the two mammogram images 50 shown in FIG. 4, obtained using a difference of Gaussians edge filter with R1=20 and R2=1. This is merely a non-limiting illustrative example.

At an operation 204 performed in parallel with the operation 202, the at least one electronic processor 20 is programmed to segment the mammogram image 50 into regions. The regions are shown in FIG. 4 in a MLO view (shown in the "left" side of FIG. 4) and a CC view (shown in the "right" side of FIG. 4). The regions can include a background region 54 and a plurality of different tissue regions such as a pectoral muscle region 56, an adipose tissue region 58, and a fibro-glandular tissue region 60. The image 50 can be segmented using any suitable segmentation algorithm known in the art. Any detected edges (that is, detected by analysis of the edge filtered image 50F) which correspond to expected edges are discarded as potential skin fold-induced edges. Such expected edges can include, for example, edges at boundaries between adjacent regions as identified by the segmentation operation 204, e.g. a skin contour and a contour of a pectoral muscle (e.g., both in cranial-caudal (CC) views and mediolateral-oblique views (MLO) of the image 50).

At an operation 206, the at least one electronic processor 20 is programmed to detect, in the edge filtered image 50F, one or more significant edges 62 that have a length exceeding a minimum length. The minimum length can be empirically optimized during training of the skin fold detection 200 on a training set of mammogram images with skin folds labeled so as to remove most short edges without discarding edges that potentially may be skin folds. As previously noted, the edge detection filter 52 may also be programmed to detect the significant edges 62 by also discarding edges delineating borders between the regions 54, 56, 58, 60.

At an operation 208, the at least one electronic processor 20 is programmed to identify a skin fold 64 as a significant edge that satisfies a skin fold criterion 66. The skin fold criterion 66 can be stored in the non-transitory computer readable medium 26. The skin fold criterion 66 can include a combination of criteria, e.g. a weighted combination. In one example, the skin fold criterion 66 is based at least in part on the region or regions 54, 56, 58, 60 a significant edge 62 intersects. In another example, the skin fold criterion 66 is based at least in part on a length of the significant edge 62. In a further example the skin fold criterion 66 is based at least in part on a contrast of the significant edge 62 in the mammogram image 50 and/or an intensity of the significant edge in the edge filtered image. A weighted combination of these three criteria may also be used, with the weights tuned by empirical training on mammogram images with labeled skin folds. An edge 62 with a high contrast in the image 50 should be an edge with high intensity in the edge filtered image. The edge detection filter 52 can assign intensity values in the edge filtered image on the intensity gradient in the image 50.

The method 200 can terminate after the operation 208, or can continue to include a mammography method 210. The mammography method 210 can include acquiring mammography images 50 in order to detect skin fold(s) 64. The at least one electronic processor 20 is programmed to control the mammography device 12 to acquire a mammography image 50. Once the image 50 is acquired, at least one electronic processor 20 is programmed to output a notification 68 (e.g., a visual notification on the display device 24, an audio notification output via a loudspeaker (not shown), and so forth) that another image should be acquired when a skin fold 64 is detected.

The method 200 can terminate after the operation 210, or can continue to include the operations 102, 104, 106, 108 of the imaging auditing workload reduction method or process 100 (the details of which will not be repeated here for brevity). For example, once multiple mammography images 50 are acquired and one or more skin fold(s) 64 are detected, the automated image quality assessment 40 is performed, in which at least one electronic processor 20 is programmed to assign quality ratings 38 to the images based on whether skin fold(s) are detected in the image(s). That is, the skin fold(s) 64 can be used in generating the manual quality ratings 38. In addition, the mammography images 50 now constitute the set 30 of images to be audited. The at least one electronic processor 20 is the programmed to: (i) generate the confidence values 42 for the images 50, (e.g., operation 102); (ii) select a subset 34 of the images for manual review based on the confidence values (e.g., operation 104); and output, on the GUI 27, the subset 34 of mammography images 50 and the manual quality ratings 46 for the mammography images respective to whether skin folds 64 are detected. The updated manual quality ratings 46 for the mammography images 50 having skin folds 64 are used to perform update training of the automatic quality assessment process 40 (e.g., operation 108).

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus for manually auditing a set of images having quality ratings for an image quality metric assigned to the respective images of the set of images by an automatic quality assessment process, the apparatus comprising:
   at least one electronic processor programmed to:
   generate quality rating confidence values indicative of confidence of the quality ratings for the respective images;
   select a first subset of the set of images for manual review based at least on the quality rating confidence values,
   combine the first subset with random sampling of the set of images to generate an augmented subset of images for manual review; and
   provide a user interface (UI) via which only the augmented subset of the set of images is presented and via which manual quality ratings for the image quality metric are received for only the subset of the set of images;
   wherein one of:
      the automatic quality assessment process assigns the quality rating for an image by comparing a threshold with a figure of merit computed for the image, and the at least one electronic processor is programmed to generate the quality rating confidence value for the image based on an absolute value of the difference between the threshold and the figure of merit for the image wherein the quality rating confidence value is monotonically nondecreasing with increasing absolute value of the difference;
      the automatic quality assessment process assigns the quality rating for an image by a process including iteratively optimizing a figure of merit computed for the image, and the at least one electronic processor is programmed to generate the quality rating confidence value for each image based on a derivative of the figure of merit for the image;
      the automatic quality assessment process assigns the quality rating for an image by a process including iteratively optimizing a figure of merit for the image, and the at least one electronic processor is programmed to generate the quality rating confidence value for each image based on a peak sharpness of the optimized figure of merit; or
      the automatic quality assessment process assigns the quality rating for an image based on a figure of merit for the image, and the at least one electronic processor is programmed to generate the quality rating confidence value for each image based on a number of local extrema of the figure of merit for the image.

2. The apparatus of claim 1, wherein the at least one electronic processor is programmed to:
   perform update training of the automatic quality assessment process using the augmented subset of the set of images and the manual quality ratings received via the UI,
   wherein update training comprises implementing a learning module to adapt the manual quality ratings to the set of images.

3. The apparatus of claim 1, wherein the automatic quality assessment process assigns the quality rating for an image by comparing a threshold with a figure of merit computed for the image, and the at least one electronic processor is programmed to:
   generate the quality rating confidence value for the image based on an absolute value of the difference between the threshold and the figure of merit for the image wherein the quality rating confidence value is monotonically nondecreasing with increasing absolute value of the difference.

4. The apparatus of claim 1, wherein the automatic quality assessment process assigns the quality rating for an image by a process including iteratively optimizing a figure of merit computed for the image, and the at least one electronic processor is programmed to:
   generate the quality rating confidence value for each image based on a derivative of the figure of merit for the image.

5. The apparatus of claim 1, wherein the automatic quality assessment process assigns the quality rating for an image by a process including iteratively optimizing a figure of merit for the image, and the at least one electronic processor is programmed to:
   generate the quality rating confidence value for each image based on a peak sharpness of the optimized figure of merit.

6. The apparatus of claim 1, wherein the automatic quality assessment process assigns the quality rating for an image based on a figure of merit for the image, and the at least one electronic processor is programmed to:
   generate the quality rating confidence value for each image based on a number of local extrema of the figure of merit for the image.

7. The apparatus of claim 1, wherein the at least one electronic processor is programmed to generate the quality rating confidence value for each image based on whether the image contains an image feature known to adversely impact accuracy of the automatic quality assessment process.

8. An apparatus, comprising:
   at least one electronic processor programmed to detect skin folds in a mammogram image by a skin fold detection method including:
      filtering the mammogram image using an edge detection filter to generate an edge filtered image;
      detecting, in the edge filtered image, one or more significant edges each having a length exceeding a minimum length; and
      identifying a skin fold as a significant edge that satisfies a skin fold criterion,
   wherein the at least one electronic processor is further programmed to perform a mammography image auditing method including:
   performing the skin fold detection method on a set of mammography images to assign quality ratings to the respective mammography images based on whether the skin folds are detected in the respective mammography images,
   generating quality rating confidence values for the quality ratings of the respective mammography images of the set of mammography images;
   selecting a subset of the set of mammography images for manual review based at least one the quality rating confidence values; and
   provide a user interface (UI) via which only the subset of the set of mammography images is presented and via which manual quality ratings for the mammography images respective to skin folds are received for only the subset of the set of mammography images.

9. The apparatus of claim 8, wherein the skin fold detection method further includes:
   segmenting the mammogram image into regions including a background region and a plurality of different tissue regions, wherein the skin fold criterion is based at least in part on the region or regions the significant edge intersects.

10. The apparatus of claim 9, wherein the plurality of different tissue regions consists of a pectoral muscle region, an adipose tissue region, and a fibro-glandular tissue region.

11. The apparatus of claim 9, wherein the detecting of the one or more significant edges includes discarding edges delineating borders between the regions.

12. The apparatus of claim 8, wherein the skin fold criterion is based at least in part on a length of the significant edge.

13. The apparatus of claim 8, wherein the skin fold criterion is based at least in part on a contrast of the significant edge in the mammogram image and/or an intensity of the significant edge in the edge filtered image.

14. The apparatus of claim 8, wherein the at least one electronic processor is further programmed to perform a mammography method including:
controlling a mammography device comprising an x ray imager to acquire the mammography image; and
output a notification indicating that another image should be acquired when the skin fold detection method identifies a skin fold.

15. An imaging method, comprising:
retrieving, for manually auditing, a set of images having quality ratings for an image quality metric assigned to the respective images of the set of images by an automatic quality assessment process;
generating quality rating confidence values indicative of confidence of the quality ratings for the respective images;
selecting a subset of the set of images for manual review based at least on the quality rating confidence values;
providing a user interface (UI) via which only the subset of the set of images is presented and via which manual quality ratings for the image quality metric are received for only the subset of the set of images; and
performing the automatic quality assessment process on the images of the set of images to assign the quality ratings to the respective images of the set of images by operations including:
for each image, applying an edge detection filter to the image to generate an edge filtered image;
detecting significant edges in the edge filtered image as edges having length greater than a minimum length; and
identifying skin folds as significant edges that satisfy a skin fold criterion, wherein the quality rating is assigned on the basis of presence or absence of identified skin folds.

\* \* \* \* \*